(12) United States Patent
McHardy et al.

(10) Patent No.: US 8,772,345 B2
(45) Date of Patent: *Jul. 8, 2014

(54) OXIMES FOR TREATMENT OF PERIPHERAL AND CENTRAL NERVOUS SYSTEM EXPOSURE TO ACETYL CHOLINESTERASE INHIBITORS

(75) Inventors: Stanton F. McHardy, San Antonio, TX (US); Richard M. Corbett, San Antonio, TX (US); Donald M. Maxwell, Baltimore, MD (US); Michael W. Tidwell, Lakehills, TX (US); Bismarck Campos, San Antonio, TX (US); Christopher J. Bemben, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/197,550

(22) Filed: Aug. 3, 2011

(65) Prior Publication Data

US 2013/0035351 A1    Feb. 7, 2013

(51) Int. Cl.
*A01N 33/24*     (2006.01)
*A61K 31/15*     (2006.01)

(52) U.S. Cl.
USPC ........... 514/640; 514/290; 514/315; 546/101; 546/246; 564/258

(58) Field of Classification Search
USPC ........... 564/258; 546/246, 101; 514/290, 315, 514/640
See application file for complete search history.

(56) References Cited

U.S. PATENT DOCUMENTS

| | | | | |
|---|---|---|---|---|
| 3,045,025 | A * | 7/1962 | Hackley et al. | ............... 546/264 |
| 5,929,093 | A | 7/1999 | Pang et al. | |
| 5,998,460 | A | 12/1999 | Brossi et al. | |
| 8,653,108 | B1 * | 2/2014 | McHardy et al. | ............. 514/331 |
| 2008/0262227 | A1 | 10/2008 | Slanina et al. | |
| 2014/0066421 | A1 * | 3/2014 | McHardy et al. | ......... 514/210.2 |

OTHER PUBLICATIONS

I. Somin et al., 2 Khimiko-Farmatsevticheskii Zhurnal 39-44 (1968).*
I. Somin et al., 13 Zhurnal Organicheskoi Khimii 910-918 (1977).*
I. Somin et al., 43 Zhurnal Obshchei Khimii 331-335 (1973).*
CAS Abstract Accession No. 1969:19526 (1969).*
H.P. Benschop et al., Med. Prot. Chem.-Warf. Agents, [Pap. Symp.] (1976), Meeting Date 1974, 120-33. Almqvist & Wiksell: Stockholm, Sweden.*
S.L. Morissette et al., Advanced Drug Delivery Reviews, 56, 275-300 (2004).*
F. Degorre et al., 31 Journal of Medicinal Chemistry, 757-763 (1988).*
A.F. Childs et al., 10 British Journal of Pharmacology, 462-465 (1955).*
Z. Kovarik et al., 175 Chemico-Biological Interactions 173-179 (2008).*
R. Odžak et al., 233 Toxicology, 85-96 (2007).*
Wang, et al., "Evaluation of the MDR-MDCK cell line as a permeability screen for the blood-brain barrier," International Journal of Pharmaceutics 288 (2005) 349-359.
Botta, et al., "Oxime Amides as a Novel Zinc Binding Group in Histone Deacetylase Inhibitors: Synthesis, Biological Activity, and Computational Evaluation," Journal of Medical Chemistry 2011, 54, 2165-2182.
Greene, "Protective Groups in Organic Chemistry," A Wiley-Interscience Publication, John Wiley & Sons, Inc. 1981 (cover page and table of contents provided).
Greene, et al., "Protective Groups in Organic Chemistry," Second Edition, A Wiley-Interscience Publication, John Wiley & Sons, Inc. 1991 (cover page and table of contents provided).
Ellman, et al; "A New and Rapid Colorimetric Determination of Acetylcholinesterase Activity"; Biochemical Pharmacology, 1961, vol. 7, pp. 88-95, Pergamon Press Ltd., printed in Great Britain.
US Office Action issued Jul. 31, 2013 issued in related U.S. Appl. No. 13/474,399 (8 pgs).

* cited by examiner

*Primary Examiner* — Deepak Rao
*Assistant Examiner* — Alexander R Pagano
(74) *Attorney, Agent, or Firm* — Grossman, Tucker et al

(57) ABSTRACT

The present invention relates to non-charged oxime compounds which are acetyl cholinesterase (AChE) reactivators of inhibited AChE and which protect against organophosphate poisoning both peripherally and in the central nervous system. Also disclosed are pharmaceutical compositions and methods for preparing the reactivator compounds and associated intermediates.

7 Claims, 5 Drawing Sheets

OXIMES FOR TREATMENT OF PERIPHERAL AND CENTRAL NERVOUS SYSTEM EXPOSURE TO ACETYL CHOLINESTERASE INHIBITORS

GOVERNMENT RIGHTS CLAUSE

This invention was made with United States Government support under Contract No. HDTRA1-10-C-0041 awarded by the Defense Threat Reduction Agency. The Government has certain rights in this invention.

FIELD OF THE INVENTION

The present invention relates to non-charged oxime compounds which are acetyl cholinesterase (AChE) reactivators of nerve-agent inhibited AChE and which protect against organophosphate poisoning both peripherally and in the central nervous systems (CNS).

BACKGROUND

Acetyl cholinesterase (AChE) is an important and essential enzyme in the body, which is responsible for the degradation or hydrolysis of acetyl choline, the neurotransmitter molecule responsible for synaptic transmission. Inhibition of AChE can cause a sharp increase in acetyl choline levels, causing overstimulation of the cholinergic system at both central and peripheral sites, resulting in the visual toxic signs commonly referred to as cholinergic crisis. Organophorus agents, such as pesticides (paraoxon, methylparaoxon, etc.) and nerve agents (Sarin, Cyclosarin, Soman, Tabun, VX, etc) represent the bulk of the major AChE inhibitor threat agents. Historically, various compounds have been proposed from the class of compounds that possess the N-alkyl bis-quaternary pyridinium moiety as a charged species. As a charged species, there may be diminished ability to penetrate the blood-brain barrier and protect against organophosphate poisoning in the brain and central nervous system (CNS).

Therefore, the invention disclosed herein has identified certain non-charged oxime based AChE reactivators with improved blood-brain barrier penetration that may be effective at reactivation of nerve agent-inhibited AChE and protect against organophosphate poisoning both peripherally and in the CNS.

SUMMARY

The present disclosure is directed at an acetyl cholinesterase (AChE) reactivator compound of the formula:

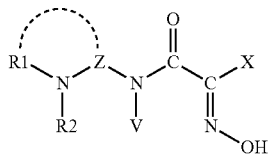

Formula I wherein
V is independently a hydrogen, alkyl (C1 to C5) groups, benzyl or substituted benzyl groups;
Z is independently an optionally substituted methylene or methine group from 1 to 8 carbon atoms in length and wherein in the case of optionally substituted methylene or methine, Z can also be connected to $R_1$ to form a heterocyclic or bicyclic heteratom ring from 3 to 10 atoms;
$R_1$ can independently be H or optionally substituted alkyl (C1 to C7), or can be connected to Z to form a heterocyclic or bicyclic heteratom ring from 3 to 10 atoms;
$R_2$ is independently H or optionally substituted alkyl (C1 to C7), benzyl or optionally substituted benzyl, phenyl, optionally substituted phenyl, heterocyclic, heteroaryl and optionally substituted heterocyclic or optionally substituted heteroaryl; and
X is independently H, cyano (CN) or COR, wherein said R group is alkyl (C1 to C3).

The present disclosure also relates to an acetyl cholinesterase reactivator compound of the formula:

Formula II

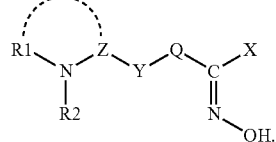

wherein:
Q is independently a carbonyl (C=O) group or a bond between Y and the oxime group;
Y is independently an optionally substituted 5- or 6-membered heterocycle or heteroaryl group;
Z is independently an oxygen, optionally substituted nitrogen or optionally substituted methylene or methine group from 1 to 8 carbon atoms in length and wherein in the case of optionally nitrogen or optionally substituted methylene or methine, Z can also be connected to $R_1$ to form a heterocyclic or bicyclic heteratom ring from 3 to 10 atoms;
$R_1$ can independently be H or optionally substituted alkyl (C1 to C7), or can be connected to Z to form a heterocyclic or bicyclic heteratom ring from 3 to 10 atoms;
$R_2$ is independently H or optionally substituted alkyl (C1 to C7), benzyl or optionally substituted benzyl, phenyl, optionally substituted phenyl, heterocyclic, heteroaryl and optionally substituted heterocyclic or optionally substituted heteroaryl;
X is independently H, cyano (CN) or COR, wherein said R group is alkyl (C1 to C3).

The present disclosure also relates to a method comprising attenuating the effects on a mammal cause by the inhibition of AChE by administering to said mammal an effective amount of a compound, or a pharmaceutically acceptable salt thereof, having the structure of Formula I and/or Formula II noted above.

DETAILED DESCRIPTION

Figure 1:
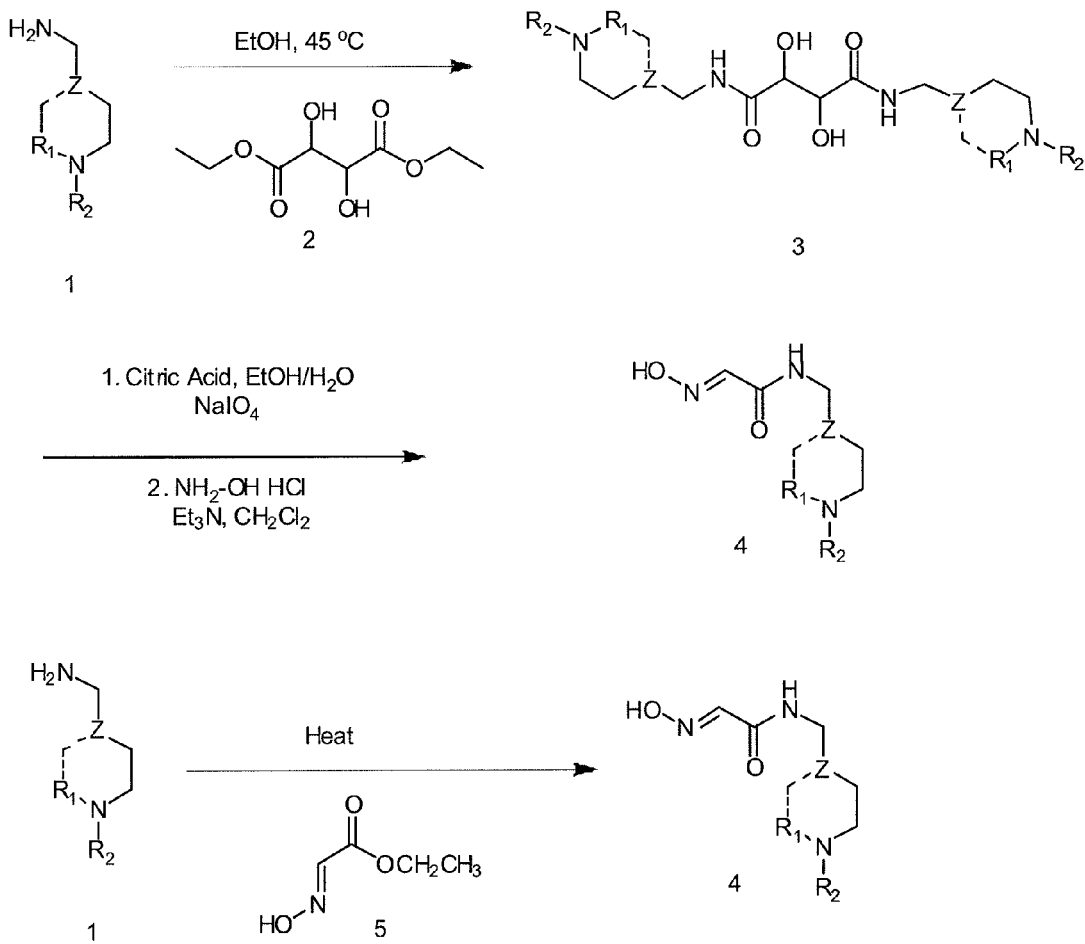
FIG. 1 illustrates two preferred methods for the preparation of AChE reactivator compounds disclosed herein.

It is to be understood that the invention is not limited in its application to the details of construction and the arrangement of components set forth in the following description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

The compounds of the present invention are directed to pharmaceutical countermeasures or antidote compositions for treating disorders or conditions associated with exposure to AChE inhibitors such as organophosphate pesticides and nerve agents. The compounds of the present invention may therefore serve as reactivators of both native and/or organophosphate-inhibited acetyl cholinesterase (AChE). Reference to a reactivator may be understood as that situation where, e.g., enzyme dephosphorylation occurs to generate the active enzyme (AChE) and is relatively faster than oxime dephosphorylation, which generates the phosphorylated enzyme.

Accordingly, the compounds of the present invention serve as reactivators of nerve agent organophosphate-inhibited human and/or mammalian acetyl cholinesterase (AChE), including AChE inhibited by Sarin, Cyclosarin (GF), Tabun, Soman, VX and other structurally related organophosphate nerve agents.

More particularly, the reactivator compounds of the present invention include compounds of Formula I below:

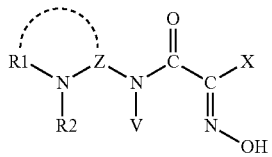

Formula I wherein:

V is independently a hydrogen, alkyl (C1 to C5) groups, benzyl or substituted benzyl groups;

Z is independently an optionally substituted methylene or methine group from 1 to 8 carbon atoms in length. In the case of optionally substituted methylene or methine, Z can also be connected to $R_1$ to form a heterocyclic or bicyclic heteratom ring from 3 to 10 atoms;

$R_1$ can independently be H or optionally substituted alkyl (C1 to C7), or can be connected to Z to form a heterocyclic or bicyclic heteratom ring from 3 to 10 atoms;

$R_2$ is independently H or optionally substituted alkyl (C1 to C7), benzyl or optionally substituted benzyl, phenyl, optionally substituted phenyl, heterocyclic, heteroaryl and optionally substituted heterocyclic or optionally substituted heteroaryl;

X is independently H, cyano (CN) or COR, wherein said R group is alkyl (C1 to C3); and wherein the oxime moiety can exist as either the E or Z isomer form. In addition, the above Formula I may be present in the form of a pharmaceutically acceptable salt.

The present invention is also directed at reactivators having the structure of Formula II:

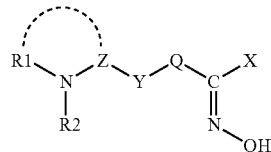

Formula II wherein:

Q is independently a carbonyl (C=O) group or a bond between Y and the oxime group;

Y is also independently an optionally substituted 5- or 6-membered heterocycle or heteroaryl group such as oxazole, triazole, imidazole, oxadiazole, pyridine, pyrimidine or pyrazine;

Z is independently an oxygen, optionally substituted nitrogen or optionally substituted methylene or methine group from 1 to 8 carbon atoms in length. In the case of optionally nitrogen or optionally substituted methylene or methine, Z can also be connected to $R_1$ to form a heterocyclic or bicyclic heteratom ring from 3 to 10 atoms;

$R_1$ can independently be H or optionally substituted alkyl (C1 to C7), or can be connected to Z to form a heterocyclic or bicyclic heteratom ring from 3 to 10 atoms;

$R_2$ is independently H or optionally substituted alkyl (C1 to C7), benzyl or optionally substituted benzyl, phenyl, optionally substituted phenyl, heterocyclic, heteroaryl and optionally substituted heterocyclic or optionally substituted heteroaryl;

X is independently H, cyano (CN) or COR, wherein said R group is alkyl (C1 to C3); and wherein the oxime moiety can exist as either the E or Z isomer form. In addition, the above Formula II may be present in the form of a pharmaceutically acceptable salt.

It may be understood that with respect to the oxime moiety, the Z designation is that situation where the two groups of higher priority (according to the Cahn-Ingold-Prelog priority rules) are on the same side of the double bond. If the two groups of higher priority are on opposite sides of the double bond, it is designated as the E isomer. In related context, the compounds of Formula I and II may also have optical centers and therefore may occur in different enantiomeric configurations. Accordingly, the general formulas identified above should be understood to preferably include all enantiomers, diastereomers and other stereoisomers of the defined compounds as well as racemic and other mixtures thereof.

As may be appreciated, the compounds herein are preferably non-charged, which may be understood as the feature where the compound itself as identified in the general formula above does not include a charged atom or functional group. As noted, this may then facilitate blood-brain barrier penetration. However, as noted, pharmaceutically acceptable salts of the compounds of Formula I and II may also be employed and include the acid addition and base salts thereof. The phrase "pharmaceutically acceptable", as used in connection with compositions of the invention, refers to molecular entities and other ingredients of such compositions that are physiologically tolerable and do not typically produce untoward reactions when administered to a mammal (e.g., human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

Some examples of pharmaceutically acceptable salt forms include, but are not limited to: acetate, adipate, aspartate, benzoate, besylate, bicarbonate/carbonate, bisulphate/sulphate, borate, citrate, formate, fumarate, gluconate, glucuronate, hexafluorophosphate, hydrochloride/chloride, hydrobromide/bromide, hydroiodide/iodide, lactate, malate, maleate, malonate, mandelates, mesylate, methylsulphate, naphthylate, 2-napsylate, nicotinate, nitrate, oxalate, palmitate, pamoate, phosphate/hydrogen phosphate/dihydrogen phosphate, pyroglutamate, salicylate, saccharate, stearate, succinate, sulfonate, stannate, tartrate, tosylate, and trifluoroacetate salts.

Suitable base salts are preferably formed from bases which form non-toxic salts. Some examples include, but are not limited to, the aluminium, calcium, choline, diethylamine, diolamine, glycine, lysine, magnesium, meglumine, olamine, potassium, sodium, and zinc salts.

The compounds of the present invention may be used as part of a combination therapy, including their administration as separate entities or combined in a single delivery system. The combination therapies may include, but are not limited to combination with an AChE inhibitor such as atropine and/or an anticonvulsant such as diazepam or midazelam.

The compounds of this invention may be preferably administered via either the oral, parenteral (such as subcutaneous, intraveneous, intramuscular, intrasternal and infusion techniques), intranasal or topical routes to mammals. In general, these compounds are most desirably administered to humans in doses ranging from about 1.0 mg to about 2000 mg per day, although variations will necessarily occur depending upon the weight and condition of the subject being treated and the particular route of administration chosen.

The compounds of the present invention may be administered alone or in combination with pharmaceutically acceptable carriers or diluents by either of the above routes previously indicated, and such administration may be carried out in single or multiple doses. More particularly, the reactivator compounds of the invention may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, organic suspensions, injectable solutions, injectable suspensions, elixirs, syrups, and the like. Such carriers may include solid diluents or fillers, sterile aqueous media and various non-toxic organic solvents, etc. Moreover, oral pharmaceutical compositions can be suitably sweetened and/or flavored. In general, the therapeutically effective compounds of this invention are present in such dosage forms at concentration levels ranging about 5.0% to about 70% by weight.

For oral administration, tablets containing various excipients such as microcrystalline cellulose, sodium citrate, calcium carbonate, dicalcium phosphate and glycine may be employed along with various disintegrants such as starch, together with granulation binders like polyvinylpyrrolidone, sucrose, gelatin and acacia. Additionally, lubricating agents such as magnesium stearate, sodium lauryl sulfate and talc are preferred for tabletting purposes. Solid compositions of a similar type may also be employed as fillers in gelatine capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions or suspensions of a compound of the present invention in either sesame or peanut oil, cotton seed oil or in aqueous propylene glycol may be employed. The aqueous solutions should be suitably buffered (preferably pH>8) if necessary and the liquid diluents first rendered isotonic. These aqueous solutions are preferred for intravenous injection purposes. The oily solutions are preferred for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The reactivator compounds of the present invention may exist in both unsolvated and solvated forms. The term 'solvate' is used herein to describe a molecular complex comprising the compound of the invention and an amount of one or more pharmaceutically acceptable solvent molecules, such as water.

The reactivator compounds of the present invention may also include isotopically labeled compounds, which are identical to those recited in the above referenced formula, but for the fact that one or more atoms are replaced by an atom having an atomic mass or mass number different from the atomic mass or mass number usually found in nature thereby allowing for improved detection and/or tracking of the compound. Examples of isotopes suitable for inclusion in the compounds of the invention include, but are not limited to, isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled reactivator compounds herein, for example, those incorporating a radioactive isotope, may be preferred in drug and/or substrate tissue distribution studies. The radioactive isotopes tritium, i.e. $^{3}H$, and carbon-14, i.e. $^{14}C$, are particularly preferred for this purpose in view of their relative ease of incorporation and ready means of detection. Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$, and $^{13}N$, may be useful in Positron Emission Topography (PET) studies for examining substrate receptor occupancy. Isotopically-labeled reactivator compounds herein may generally be prepared by conventional techniques known to those skilled in the art or by processes analogous to those described in the accompanying examples and preparations using an appropriate isotopically-labeled reagent in place of the non-labeled reagent previously employed.

Reactivator compounds of Formula I herein were assessed for affinity and reactivation of nerve agent-inhibited recombinant human AChE. Reactivation studies were conducted with commercially obtained recombinant human AChE and assayed by a robotic spectrophotometric assay using acetylthiocholine as substrate at pH 7.4 and 25° C. via the procedure established by Ellman (*Biochem Pharmacol* 1961, 7, 88-95). The time-course of reactivation of nerve agent-inhibited AChE was determined by adding various concentrations of reactivator compounds of the above-referenced formula to agent-inhibited AChE. Samples of the compound/inhibited AChE mixture were removed at sequential times to measure the compound-induced recovery of AChE activity. The time-course of AChE reactivation at each compound concentration [OX] was analyzed kinetically as a pseudo first-order reaction. The observed first-order reaction constant ($k_{obs}$) was fitted to the Michaelis-Menten function:

$$k_{obs}=kr[OX]/(KD+[OX])$$

where kr is the maximal first-order reactivation rate constant for the reactivator compound considered and 1/KD is its affinity for AChE. In vitro reactivation studies were conducted against AChE that has been inhibited with the nerve agent GF (cyclosarin). Reactivator compounds of the herein referenced general formula within this invention showed 10-80% reactivation of GF-inhibited human AChE at concentrations from 500 nM to 1 mM and time points from 8 to 240 minutes.

The reactivator compounds of Formula I may preferably be prepared by the methods described below, together with synthetic methods known in the art of organic chemistry, or modifications and derivatisations that are familiar to those of ordinary skill in the art. During any of the following synthetic sequences it may be preferred and/or desirable to protect sensitive or reactive groups on any of the molecules concerned. This can be achieved by means of conventional protecting groups, such as those described in T. W. Greene, *Protective Groups in Organic Chemistry*, John Wiley & Sons, 1981; and T. W. Greene and P. G. M. Wuts, *Protective Groups in Organic Chemistry*, John Wiley & Sons, 1991, which are hereby incorporated by reference.

Figure 2:
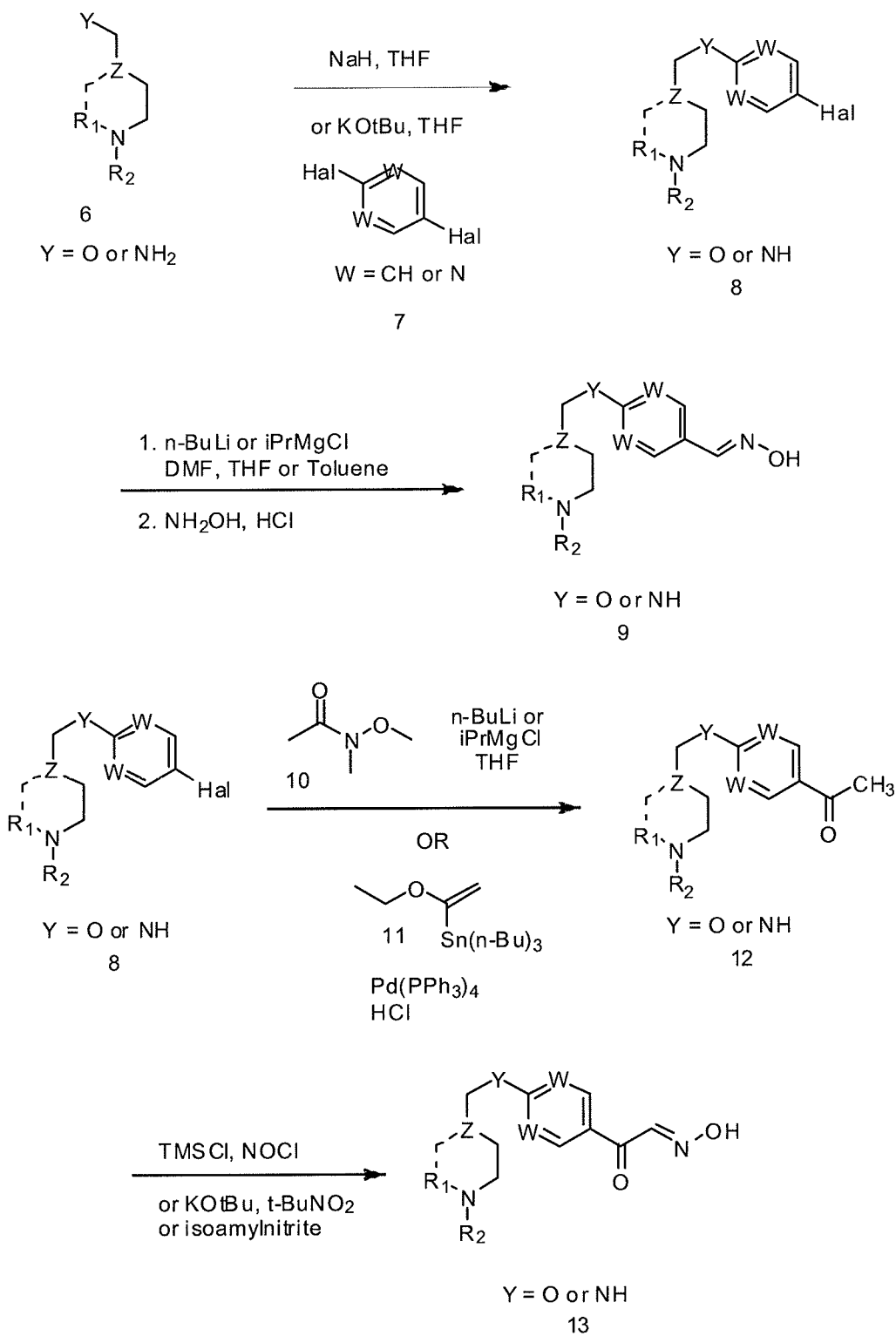
FIG. 2 illustrates two additional preferred methods for preparation of the AChE reactivator compounds disclosed herein.

Reactivator compounds of Formula I and/or their pharmaceutically acceptable salts may preferably be prepared according to the following reaction Schemes I and II as discussed herein and respectively illustrated in FIGS. 1 and 2. Isolation and purification of the products may be accomplished by standard procedures, which are known to a chemist of ordinary skill. The following schemes and discussion are exemplary of the processes for making compounds of general formula I. It is to be understood, however, that the synthetic scheme, as fully described herein, is not intended to be limited by the details of the following examples.

FIG. 1 illustrates two preferred methods for the preparation of reactivator compounds having the basic structure of the above referenced general formula, where Z, $R_1$ and $R_2$ are defined as above. Referring to FIG. 1, compounds of formula I can be purchased or prepared using synthetic methods known in the art of organic chemistry, or modifications and derivatisations that are familiar to those of ordinary skill in the art. Referring to FIG. 1, an amine of formula 1 can be treated with a tartrate ester such as compound 2 in an alcoholic solvent such as ethanol or methanol, at temperatures ranging from room temperature to 75° C., preferably at or around 45° C., to provide the dimeric amide of general formula 3. Compounds of formula 3 can then be treated under acidic sodium periodate conditions in solvents such as alcohol or water, preferably ethanol and water, to provide the intermediate amide-aldehyde (not depicted), which can then be immediately reacted with hydroxylamine hydrochloride, alone or in the presence of a tertiary amine base, such as triethylamine, to produce the desired compounds of formula 4. An alternative method for the preparation of compounds of formula 4 is also described in FIG. 1. Compounds of formula 1 can be treated with the gloxylate oximes, such as ethyl 2-(hydroxyimino) acetate 5 in a suitable solvent such as ethanol, DMF or acetonitrile, or reacted neat with the compound of formula 1, at temperatures ranging from room temperature to 150° C., preferably at about 80° C., to produce the desired amide-oxime compounds of formula 4.

FIG. 2 illustrates another preferred method for the preparation of reactivator compounds having the general formula above, where Y, Z, $R_1$ and $R_2$ are defined as above, Y is an oxygen or nitrogen atom of appropriate substitution, W is independently CH (methine) or N (nitrogen) and 'Hal' represents halogen groups, such as fluoride, chloride, bromide or iodide. Referring to FIG. 2, an alcohol or amine of formula 6 can be reacted with a di-halogenated heterocyclic compound of formula 7 to form the desired heteroaryl ether or heteroaryl amine of formula 8. Conditions for this reaction include the use of a suitable base such as sodium hydride (NaH) or potassium tert-butoxide (KOtBu) in solvents such as tetrahydrofuran (THF) or diethyl ether, at temperatures ranging from room temperature to 100° C., preferably around 60° C., to provide the desired compounds of formula 8. Treatment of compounds of formula 8 with a suitable Grignard reagent or organolithium reagent, such as Isopropyl magnesium chloride (iPrMgCl) or n-butyl lithium (n-BuLi) and dimethylformamide, in solvents such as toluene, THF or ether, at temperatures ranging from −100° C. to room temperature, provides the corresponding aldehyde (not depicted), which can then be immediately reacted with hydroxylamine hydrochloride, in a solvent such as ethanol or dichloromethane, alone or in the presence of a tertiary amine base, such as triethylamine, to produce the desired oxime compounds of formula 9.

As also illustrated in FIG. 2, ketone compounds of formula 12 can also be prepared from the compounds of formula 8 via two methods. Treatment of compounds of formula 8 with a suitable Grignard reagent or organolithium reagent, such as Isopropyl magnesium chloride (iPrMgCl) or n-butyl lithium (n-BuLi) and the Weinreb amide 10, in solvents such as toluene, THF or ether, at temperatures ranging from −100° C. to room temperature, provides the corresponding ketone compounds of formula 12. Alternatively, compounds of formula 8 can be coupled with the vinyl stannane reagent 11, utilizing a suitable catalyst such as tetrakistriphenylphosphine palladium (0), to produce the corresponding vinyl ether (not depicted), which can be hydrolyzed with HCl to produce the ketone compounds of formula 12. Ketone compounds of formula 12 can be reacted under a variety of conditions to produce the desired keto-oxime compounds of formula 13. Suitable conditions for this transformation include trimethylsilyl chloride and nitrosyl chloride, potassium tert-butoxide and tert-butyl nitrite (tBuNO$_2$) or isoamyl nitrite.

Figure 3:
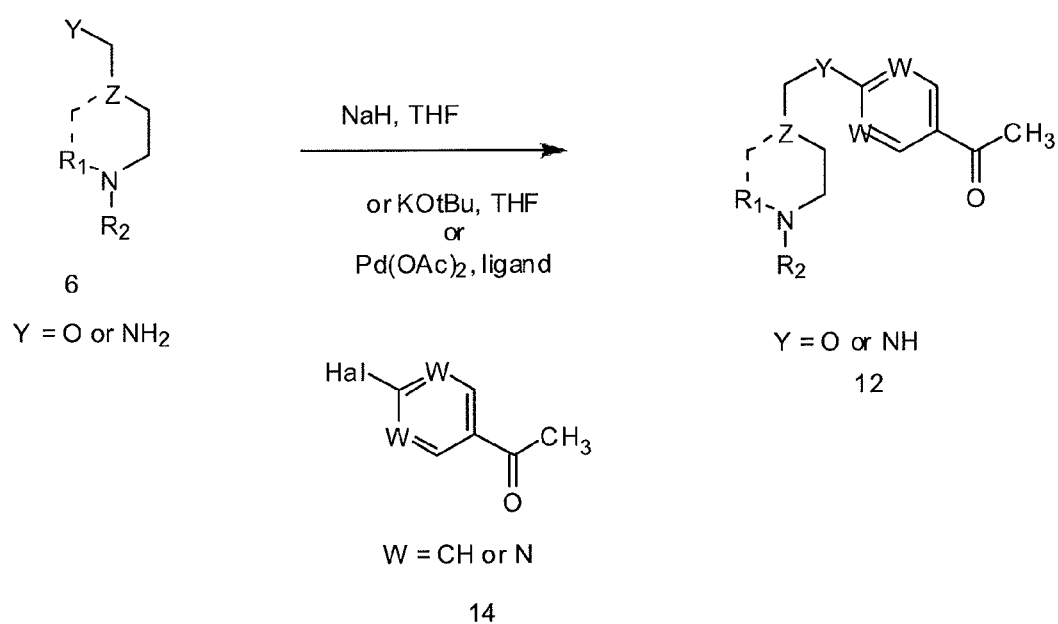
FIG. 3 illustrates a preferred method for the synthesis of the intermediate 12 identified in FIG. 2.

As illustrated in FIG. 3, a method is identified for the synthesis of the intermediate 12 prepared above in FIG. 2. Referring to FIG. 3, an alcohol or amine of general formula 6 can be reacted with a halogenated-methyl ketone heterocyclic compound of general formula 14 to form the desired heteroaryl ether or heteroaryl amine of general formula 12. Conditions for this reaction include the use of a suitable base such as sodium hydride (NaH) or potassium tert-butoxide (KOtBu) in solvents such as tetrahydrofuran (THF) or diethyl ether, at temperatures ranging from room temperature to 100° C., preferably around 60° C., to provide the desired compounds of general formula 12. Other conditions for this transformation involve the use of a suitable palladium catalyst, such as Pd(OAc)$_2$ and a ligand, in solvent such as DMF or THF. Intermediate 12 can be taken on to the desired compounds of Formula II as described above in FIG. 2.

Figure 4:
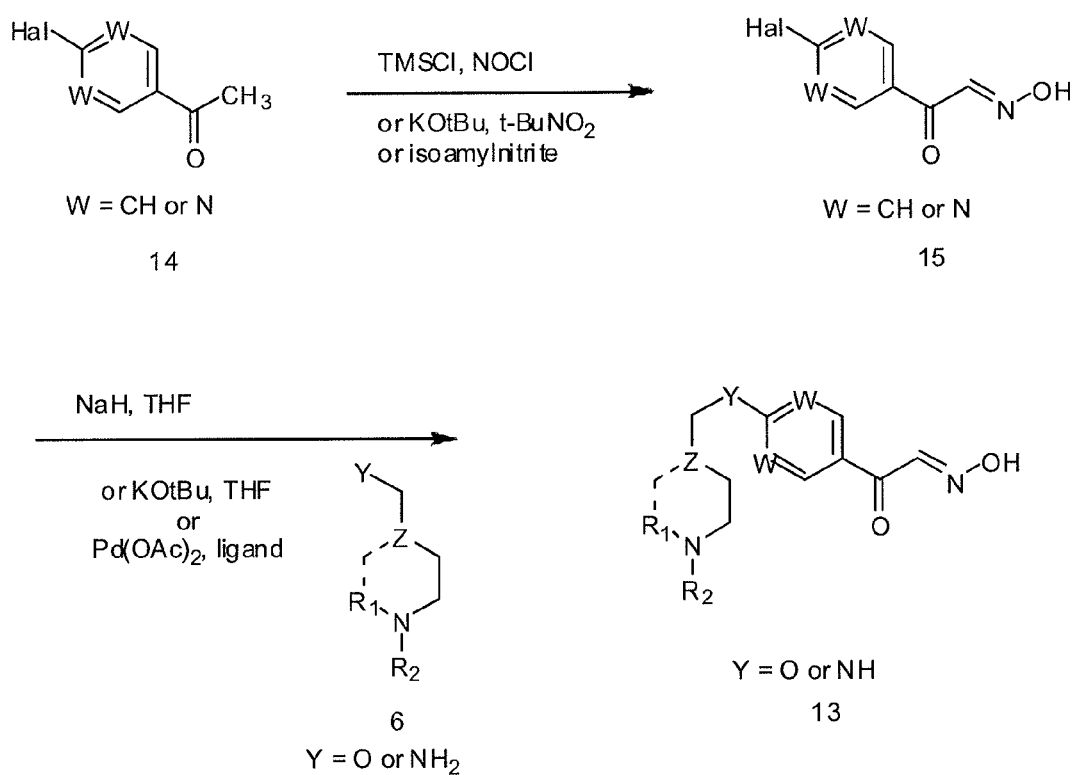
FIG. 4 illustrates a preferred method for the synthesis of compound 13 prepared in FIG. 2.

FIG. 4 identifies another method for the synthesis of the compound of general formula 13, prepared above in FIG. 2. Referring to FIG. 4, a halogenated heteroaryl ketone of general formula 14 can be reacted under a variety of conditions to produce the desired keto-oxime intermediate of general formula 15. Suitable conditions for this transformation include trimethylsilyl chloride and nitrosyl chloride, potassium tert-butoxide and tert-butyl nitrite (tBuNO$_2$) or isoamyl nitrite. Compound 15 can then be reacted with the alcohol or amine of general formula 6, under similar conditions to those described above for compound 12 above (Scheme III) to provide the desired compounds of general formula 13.

Figure 5:
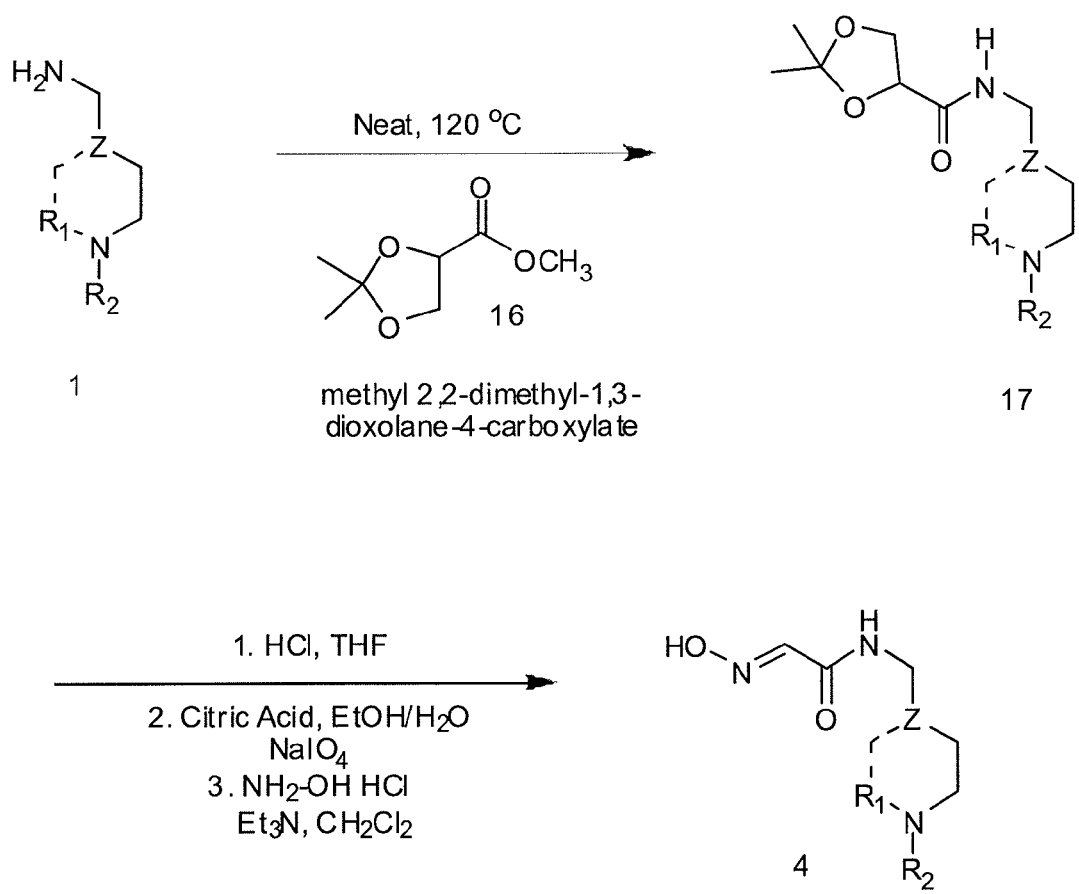
FIG. 5 illustrates a preferred method for the synthesis of the compound of compound 4 in FIG. 1.

FIG. 5 identifies yet another method for the synthesis of the compound of general formula 4, prepared above in FIG. 1. Referring to FIG. 5, an amine of general formula 1 can be treated with methyl 2,2-dimethyl-1,3-dioxolane-4-carboxylate, 16 neat at temperatures ranging from room temperature to 130° C., preferably at or around 120° C., to provide the amide of general formula 17. Compounds of formula 17 can then be treated under HCl/THF or other suitable acidic conditions to deprotect the acetonide moiety and provide the desired diol (not depicted). Treatment of the diol with acidic sodium periodate conditions in solvents such as alcohol or water, preferably ethanol and water, to provide the intermediate amide-aldehyde (not depicted), which can then be immediately reacted with hydroxylamine hydrochloride, alone or in the presence of a tertiary amine base, such as triethylamine, to produce the desired compounds of general formula 4.

Finally, compounds of Formula I and II prepared in FIGS. 1-5 may have a pharmaceutically acceptable salt form prepared under standard conditions by one skilled in the art. As a representative example, amide-oxime and keto-oxime compounds of formulas 4, 9 or 13 (FIGS. 1 and 2) can be dissolved in a suitable solvent such as methanol, ethanol, dichloromethane, ethyl acetate or isopropyl acetate and treated with a suitable acid, such as an anhydrous solution of HCl in ether, to produce the corresponding hydrochloric acid salt form.

The following examples were prepared according to the schemes identified in FIGS. 1-5 and the description provided herein.

| Example | Structure | IUPAC Name |
|---|---|---|
| Example 1 | 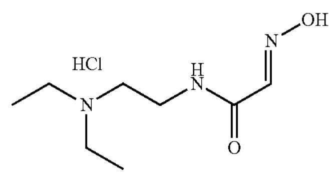 | N-(2-(diethylamino)ethyl)-2-(hydroxyimino)acetamide hydrochloride |
| Example 2 | 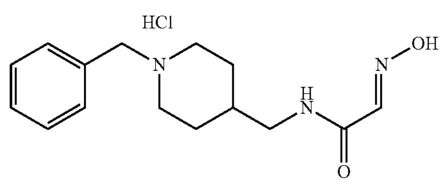 [SMILES: Cl ; O=C(/C=N/O)NCC1CCN(Cc2ccccc2)CC1] | N-((1-benzylpiperidin-4-yl)methyl)-2-(hydroxyimino)acetamide hydrochloride |
| Example 3 | 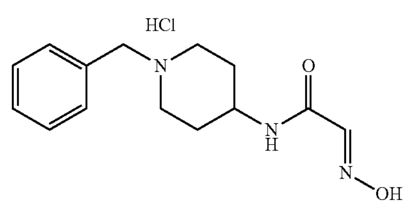 [SMILES: Cl ; O=C(/C=N/O)NC1CCN(Cc2ccccc2)CC1] | N-(1-benzylpiperidin-4-yl)-2-(hydroxyimino)acetamide hydrochloride |
| Example 4 | 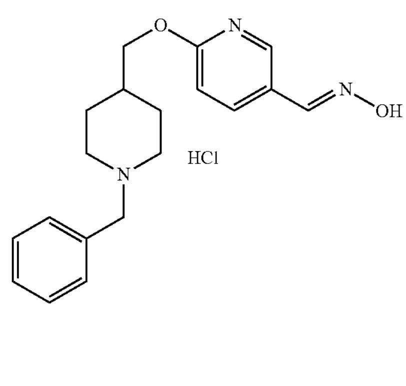 [SMILES: O/N=C/c1ccc(OCC2CCN(Cc3ccccc3)CC2)nc1 ; Cl] | 6-((1-benzylpiperidin-4-yl)methoxy)nicotinaldehyde oxime hydrochloride |

| Example | Structure | IUPAC Name |
| --- | --- | --- |
| Example 5 | 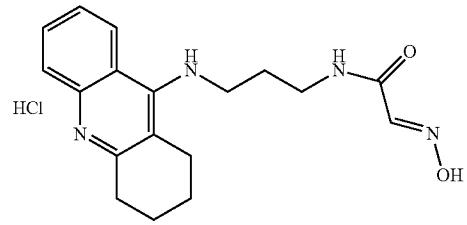 [SMILES: Cl ; O=C(/C=N/O)NCCCNc1c2c(nc3ccccc13)CCCC2] | 2-(hydroxyimino)-N-(3-(1,2,3,4-tetrahydroacridin-9-ylamino)propyl)acetamide hydrochloride |
| Example 6 | 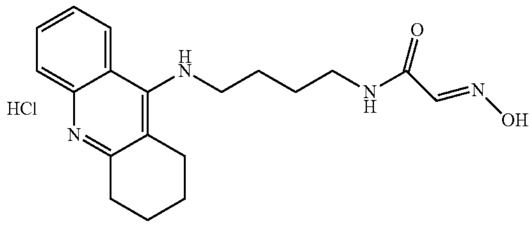 [SMILES: Cl ; O=C(/C=N/O)NCCCCNc1c2c(nc3ccccc13)CCCC2] | 2-(hydroxyimino)-N-(4-(1,2,3,4-tetrahydroacridin-9-ylamino)butyl)acetamide hydrochloride |
| Example 7 | 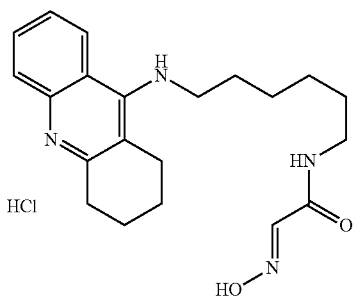 [SMILES: Cl ; O=C(/C=N/O)NCCCCCCNc1c2c(nc3ccccc13)CCCC2] | 2-(hydroxyimino)-N-(6-(1,2,3,4-tetrahydroacridin-9-ylamino)hexyl)acetamide hydrochloride |
| Example 8 | 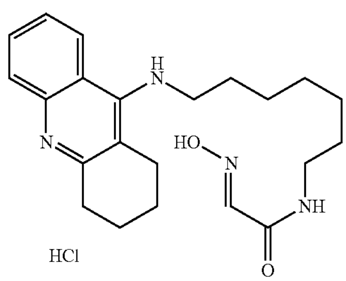 [SMILES: O=C(/C=N/O)NCCCCCCCNc1c2c(nc3ccccc13)CCCC2 ; Cl] | 2-(hydroxyimino)-N-(7-(1,2,3,4-tetrahydroacridin-9-ylamino)heptyl)acetamide hydrochloride |
| Example 9 | 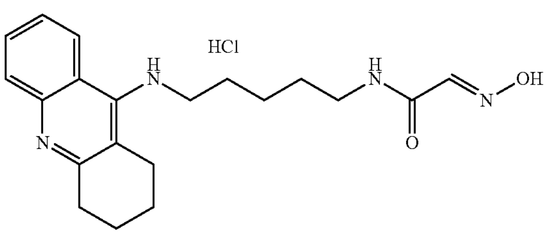 [SMILES: O=C(/C=N/O)NCCCCCNc1c2c(nc3ccccc13)CCCC2 ; Cl] | 2-(hydroxyimino)-N-(5-(1,2,3,4-tetrahydroacridin-9-ylamino)pentyl)acetamide hydrochloride |
| Example 10 | 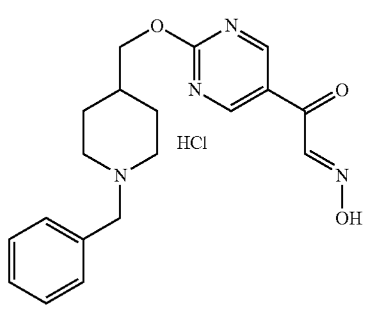 [SMILES: O=C(/C=N/O)c1cnc(OCC2CCN(Cc3ccccc3)CC2)nc1 ; Cl] | 2-(2-((1-benzylpiperidin-4-yl)methoxy)pyrimidin-5-yl)-2-oxoacetaldehyde oxime hydrochloride |

-continued

| Example | Structure | IUPAC Name |
|---|---|---|
| Example 11 | 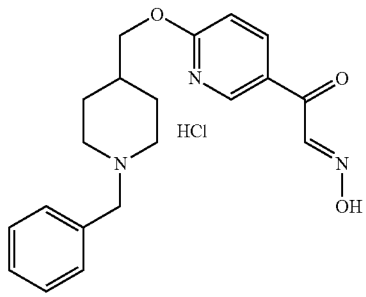 [SMILES: O=C(/C=N/O)c1ccc(OCC2CCN(Cc3ccccc3)CC2)nc1 ; Cl] | 2-(6-((1-benzylpiperidin-4-yl)methoxy)pyidin-3-yl)-2-oxoacetaldehyde oxime hydrochloride |
| Example 12 | 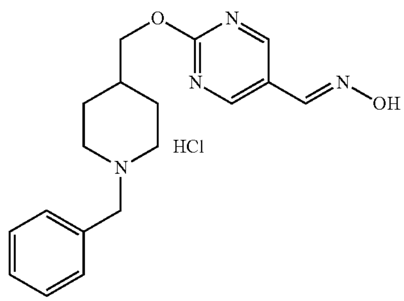 [SMILES: O/N=C/c1cnc(OCC2CCN(Cc3ccccc3)CC2)nc1 ; Cl] | 2-((1-benzylpiperidin-4-yl)methoxy)pyrimidine-5-carbaldehyde oxime hydrochloride |
| Example 13 | 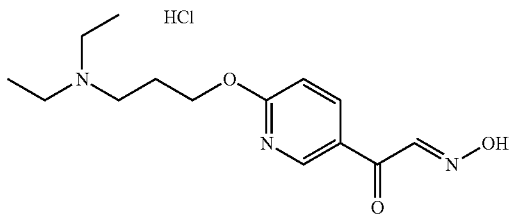 [SMILES: CCN(CC)CCCOc1ccc(C(=O)/C=N/O)cn1 ; Cl] | 2-(6-(3-(diethylamino)propoxy)pyridin-3-yl)-2-oxoacetaldehyde oxime hydrochloride |
| Example 14 | 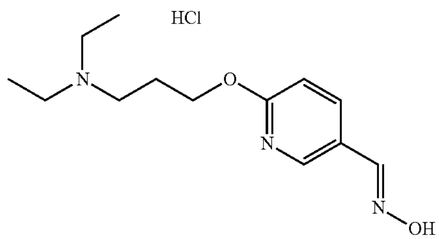 [SMILES: CCN(CC)CCCOc1ccc(/C=N/O)cn1 ; Cl] | 6-(3-(diethylamino)propoxy)nicotinaldehyde oxime hydrochloride |
| Example 15 | 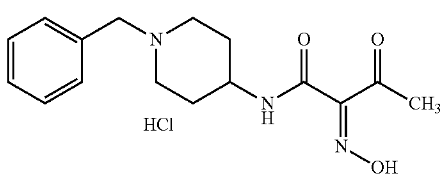 [SMILES: CC(=O)/C(=N\O)C(=O)NC1CCN(Cc2ccccc2)CC1 ; Cl] | N-(1-benzylpiperidin-4-yl)-2-(hydroxyimino)-3-oxobutanamide hydrochloride |
| Example 16 | 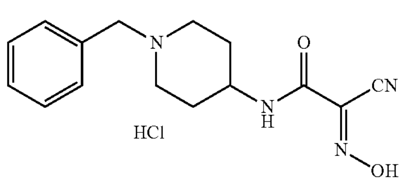 [SMILES: N#C/C(=N\O)C(=O)NC1CCN(Cc2ccccc2)CC1 ; Cl] | 2-(1-benzylpiperidin-4-ylamino)-N-hydroxy-2-oxoacetimidoyl cyanide hydrochloride |

| Example | Structure | IUPAC Name |
|---|---|---|
| Example 17 | 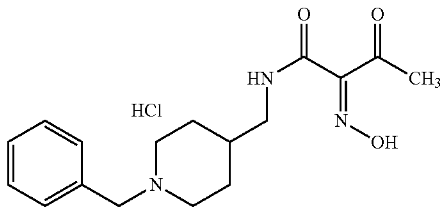 [SMILES: CC(=O)/C(=N\O)C(=O)NCC1CCN(Cc2ccccc2)CC1 ; Cl] | N-((1-benzylpiperidin-4-yl)methyl)-2-(hydroxyimino)-3-oxobutanamide hydrochloride |
| Example 18 | 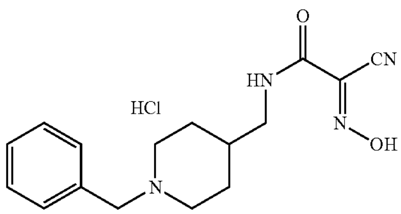 [SMILES: N#C/C(=N\O)C(=O)NCC1CCN(Cc2ccccc2)CC1 ; Cl] | 2-((1-benzylpiperidin-4-yl)methylamino)-N-hydroxy-2-oxoacetimidoyl cyanide hydrochloride |
| Example 19 | 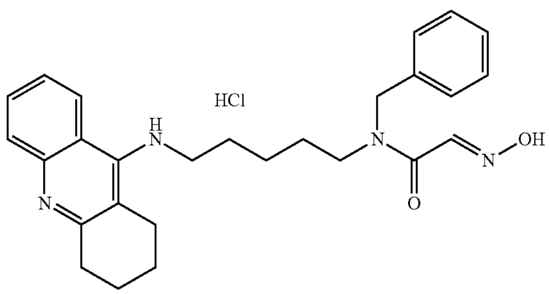 [SMILES: O=C(/C=N/O)N(CCCCCNc1c2c(nc3ccccc13)CCCC2)Cc1ccccc1 ; Cl] | N-benzyl-2-(hydroxyimino)-N-(5-(1,2,3,4-tetrahydroacridin-9-ylamino)pentyl)acetamide hydrochloride |

MDR/MDCK Assay Description and Data

Compounds within this invention were screened in the MDR/MDCK assay, which has been found to be a reasonable in vitro predictor for efflux activity associated with the blood-brain barrier. See, Wang, Q. et al, *Evaluation of the MDR-MDCK Cell Line As a Permeability Screen For The Blood Brain Barrier*, Int. J. Pharm. 2005, 288(2) 349-359. The assay is a bidirectional assay in a transwell format system, assessing the permeability of compounds across a Madin Darby canine kidney cell line transfected with human MDR-1 gene. Efflux is assessed based on ratios from the basolateral and apical sides of the chamber.

The MDR/MDCK data for select compounds is highlighted in Table I below. As can be seen, the compounds herein demonstrate a range of brain penetration classifications.

TABLE I

| Compound | Papp ($\times 10^{-6}$ cm/s) A-B | B-A | Efflux | Brain Penetration Classification |
|---|---|---|---|---|
| N-((1-benzylpiperidin-4-yl)methyl)-2-(hydroxyimino)acetamide hydrochloride | 3.19 | 19.8 | 6.2 | Moderate |
| N-(2-(diethylamino)ethyl)-2-(hydroxyimino)acetamide hydrochloride | <0.51 | <0.67 | ND | Low |
| 2-(hydroxyimino)-N-(3-(1,2,3,4-tetrahydroacridin-9-ylamino)propyl)acetamide hydrochloride | 0.21 | 4.37 | 21 | Low |
| 2-(hydroxyimino)-N-(5-(1,2,3,4-tetrahydroacridin-9-ylamino)pentyl)acetamide hydrochloride | 0.3 | 7.92 | 26 | Low |
| 2-(2-((1-benzylpiperidin-4-yl)methoxy)pyrimidin-5-yl)-2-oxoacetaldehyde oxime hydrochloride | 9.2 | 12.3 | 1.3 | High |
| 2-(6-((1-benzylpiperidin-4-yl)methoxy)pyridin-3-yl)-2-oxoacetaldehyde oxime hydrochloride | 13.5 | 9.54 | 0.7 | High |
| 2-((1-benzylpiperidin-4-yl)methylamino)-N-hydroxy-2-oxoacetimidoyl cyanide hydrochloride | 0.07 | 0.44 | 5.9 | Low |
| N-((1-benzylpiperidin-4-yl)methyl)-2-(hydroxyimino)-3-oxobutanamide hydrochloride | 17.4 | 21.3 | 1.2 | High |
| 2-(6-(3-(diethylamino)propoxy)pyridin-3-yl)-2-oxoacetaldehyde oxime hydrochloride | 6.46 | 18.6 | 2.9 | High |

TABLE I-continued

| Compound | Papp (×10⁻⁶ cm/s) A-B | B-A | Efflux | Brain Penetration Classification |
|---|---|---|---|---|
| 1,1'-methylenebis(4-(hydroxyimino)methyl)pyridinium)methanesulfonate (MMB4 DMS-Control bis-pyridinium) | <0.57 | <0.57 | ND | Low |

What is claimed is:

1. A pharmaceutical composition comprising:
   (a) an acetyl cholinesterase reactivator compound of a formula:

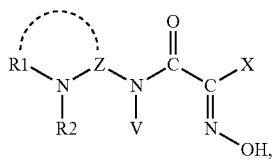

or a pharmaceutically acceptable salt thereof, in an amount ranging from 1.0 mg to 2,000 mg,
   wherein V is independently a hydrogen, an alkyl (C1 to C5) group, or a benzyl or substituted benzyl group;
   Z is independently an optionally substituted methylene or methine group from 1 to 8 carbon atoms in length, and wherein in the case of optionally substituted methylene or methine, Z can also be connected to $R_1$ to form a heterocyclic or bicyclic heteratom ring from 3 to 10 atoms;
   $R_1$ can independently be H or optionally substituted alkyl (C1 to C7), or can be connected to Z to form a heterocyclic or bicyclic heteratom ring from 3 to 10 atoms;
   $R_2$ is independently H or optionally substituted alkyl (C1 to C7), benzyl or optionally substituted benzyl, phenyl, optionally substituted phenyl, heterocyclic, heteroaryl and optionally substituted heterocyclic or optionally substituted heteroaryl; and
   X is independently H, cyano (CN) or COR, wherein said R group is alkyl (C1 to C3); and
   (b) a pharmaceutically acceptable buffered aqueous carrier solution,
   wherein the pH of the pharmaceutical composition is greater than 8 and wherein the pharmaceutical composition is sterile.

2. The pharmaceutical composition of claim 1, wherein the acetyl cholinesterase reactivator compound is present as the E or Z isomer with respect to the oxime moiety.

3. The pharmaceutical composition of claim 1, wherein said pharmaceutically acceptable salt is selected from the group consisting of acetate, adipate, aspartate, benzoate, besylate, bicarbonate/carbonate, bisulphate/sulphate, borate, citrate, formate, fumarate, gluconate, glucuronate, hexafluorophosphate, hydrochloride/chloride, hydrobromide/bromide, hydroiodide/iodide, lactate, malate, maleate, malonate, mandelates, mesylate, methylsulphate, naphthylate, 2-napsylate, nicotinate, nitrate, oxalate, palmitate, pamoate, phosphate/hydrogen phosphate, di hydrogen phosphate, pyroglutamate, salicylate, saccharate, stearate, succinate, sulfonate, stannate, tartrate, tosylate, and trifluoroacetate.

4. The pharmaceutical composition of claim 1, wherein said pharmaceutically acceptable salt is selected from the group consisting of aluminum, calcium, choline, diethylamine, diolamine, glycine, lysine, magnesium, meglumine, olamine, potassium, sodium, and zinc.

5. The pharmaceutical composition of claim 1, wherein said acetyl cholinesterase reactivator compound is isotopically labeled.

6. The acetyl cholinesterase reactivator compound of claim 5 wherein said isotopic labeling comprises labeling with one or more of the following: $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$.

7. A method for reactivating acetyl cholinesterase in a mammal comprising administering to said mammal an effective amount of a pharmaceutical composition according to claim 1.

* * * * *